United States Patent
Saito et al.

(10) Patent No.: US 7,351,531 B2
(45) Date of Patent: Apr. 1, 2008

(54) MOLECULES CAPABLE OF BINDING TO TELOMERE AND THE LIKE AND METHOD WITH THE USE OF THE SAME

(75) Inventors: Isao Saito, Kyoto (JP); Kazuhiko Nakatani, Uji (JP); Shinsuke Sando, Kyoto (JP)

(73) Assignee: Japan Science and Technology Corporation, Saitama (JP)

( * ) Notice: Subject to any disclaimer, the term of this patent is extended or adjusted under 35 U.S.C. 154(b) by 718 days.

(21) Appl. No.: 10/333,152

(22) PCT Filed: Jul. 17, 2001

(86) PCT No.: PCT/JP01/06150

§ 371 (c)(1),
(2), (4) Date: Jan. 16, 2003

(87) PCT Pub. No.: WO02/06282

PCT Pub. Date: Jan. 24, 2002

(65) Prior Publication Data

US 2004/0170980 A1 Sep. 2, 2004

(51) Int. Cl.
*C12Q 1/68* (2006.01)
*C07H 21/00* (2006.01)
*C07H 21/02* (2006.01)

(52) U.S. Cl. .................. 435/6; 536/23.1; 536/24.3
(58) Field of Classification Search .............. 435/6; 536/23.1, 24.3
See application file for complete search history.

(56) References Cited

FOREIGN PATENT DOCUMENTS

| EP | 1 164 202 A1 | 12/2001 |
|---|---|---|
| JP | 2000-239252 | 9/2000 |
| JP | 2001-89478 | 4/2001 |
| JP | 2001-149096 | 6/2001 |

OTHER PUBLICATIONS

Murray et al. "7-Amido-1,8-naphthyridines as hydrogen bonding units for the complexation of guanine derivatives: the role of 2-alkoxyl groups in decreasing binding affinity" Tetrahedron Letters vol. 36, No. 42, pp. 7627-7630, 1995.*

Gianfranco Chiarelotto, Maria Grazia Ferlin, Daniela Vedaldi, Francesco Dall'Acqua, and Giovanni Rodighiero; New mono-and bis-intercalculating compounds between DNA base pairs, *Il Farmaco*, 1993 vol. 48, No. 6, p. 835-855.

T.K. Chen et al., "Diacridines, Bifunctional Intercalators, Chemistry and Antitumor Activity", *Journal of Medicinal Chemistry*, American Chemical Society, Washington, US, vol. 21, No. 9, pp. 868-874 (1978).

B. Gaugain et al., "DNA Bifunctional Intercalators. Synthesis and Conformational Properties of an Ethidium Homodimer and of an Acridine Ethidium Heterodimer", *Biochemistry*, American Chemical Society, Easton, PA, US, vol. 17, No. 24, pp. 5071-5078 (Nov. 28, 1978).

W.M. Dai et al., "Bifunctional 2-Naphthyl Propargylic Sulfones Exhibiting High DNA Intercalating and Alkylating Activity", *Bioorganic & Medicinal Chemistry Letters*, Oxford, GB, vol. 9, No. 19, pp. 2789-2794 (Oct. 4, 1999).

* cited by examiner

*Primary Examiner*—Jezia Riley
(74) *Attorney, Agent, or Firm*—Peter F. Corless; Christine C. O'Day; Edwards Angell Palmer & Dodge LLP

(57) ABSTRACT

A method of forming a self-connective structure (a hairpin structure, a four-stranded structure, etc.) of a single-stranded oligonucleotide chain by forming a mimetic base pair of a mismatch base pair failing to form any normal base pair among base pairs of the single-stranded oligonucleotide chain with the use of a compounds represented by the following general formula (I): A-L-B (I) wherein A represents a chemical structural moiety capable of forming a pair with one base of a base pair failing to form any normal base pair; B represents a chemical structural moiety capable of forming a pair with the other base of the base pair failing to form any normal base pair; and L represents a linker structure by which the chemical structures A and B are linked to each other; and a method of inhibiting the activity of enzyme according to the previous method.

11 Claims, 5 Drawing Sheets

Mispair Recognition Complex

Mismatch DNA

SEQUENCE LISTING

```
<160> NUMBER OF SEQ ID NOS: 9

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttagggttag gg                                                         12

<210> SEQ ID NO 2
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 accgt                                                                  5

<210> SEQ ID NO 3
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 acagt                                                                  5

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4 tcgga                                                                     5

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 acggt                                                                     5

<210> SEQ ID NO 6
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 acggt                                                                     5

<210> SEQ ID NO 7
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 tcgga                                                                     5

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttagggttag ggttag                                                        16

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agggttaggg ttagggttag gg                                                 22
```

MOLECULES CAPABLE OF BINDING TO TELOMERE AND THE LIKE AND METHOD WITH THE USE OF THE SAME

TECHNICAL FIELD

The present invention relates to a method of forming a self-connective structure such as a hairpin structure of a single-stranded oligonucleotide chain by forming a mimetic base pair of a mismatch base pair that fails to form any normal base pair among the base pairs of the single-stranded oligonucleotide chain by the use of base pair mismatch recognition molecule compounds represented by the following general formula (I):

A—L—B     (I)

wherein A represents a chemical structural moiety capable of forming a pair with one base of a base pair that fails to form a normal base pair; B represents a chemical structural moiety capable of forming a pair with the other base of that base pair failing to form a normal base pair; and L represents a linker structure that binds the chemical structures A and B; to a method of stabilizing the self-connective structure such as a hairpin structure or a four-stranded (quadraplex) structure of a single-stranded oligonucleotide chain according to the above-mentioned method and to a stabilizer for the method; and to a method of forming the self-connective structure such as a hairpin structure of a single-stranded oligonucleotide chain according to the above-mentioned method to thereby inhibit the activity of an enzyme that synthesizes a complementary chain to the single-stranded oligonucleotide chain, to the enzyme activity inhibitor and to a pharmaceutical composition that comprises a compound of formula (I) mentioned above.

More concretely, the invention relates to a method of inhibiting cancer cell division, which comprises acting the base pair mismatch recognition molecule of formula (I) of the invention on a part of the single-stranded DNA at the 3'-terminal of chromosome to form a self-connective structure such as a hairpin structure in the single-stranded DNA part to thereby retard telomere extension by telomerase, and relates to a pharmaceutical composition for it.

BACKGROUND ART

Telomere is a part of DNA that exists at the end of chromosome. In the initial stage of a human chromosome gene that comprises repetitive sequences of TTAGGG, telomere is a DNA having a length of about 10 kb. Various types of proteins bind to telomere, which therefore acts to prevent the ends of DNAs from bonding to each other to form a cyclic DNA, or acts to bond to nuclear membranes. A majority of telomere is double-stranded, but several tens of bases at the outermost 3'-terminal end protrude as single-stranded.

In cell division, DNAs are replicated. In the replication mechanism, however, the replicated RNA primer moiety is not substituted with DNA in every replication, and therefore the 5'-terminal side telomere is shortened. At the same time, the 5'-terminal side including the parent DNA that has been the template for the replication is modified, and, as a result, the telomere moiety of both the parent DNA and the child DNA is shortened after the DNA replication. This was reported in 1972 in theory, and in 1989, it was clarified that the telomere moiety is shortened by about 50 to 150 bases or so in every DNA replication. When the length of the telomere moiety becomes about 5 kb or so, the cell division life thereof comes to an end (M1 stage) and no more cell division occurs. In normal cells, TRF1, a type of telomere-binding protein binds to the double-stranded (duplex) part of telomere, and it inhibits telomere extension. After having reached the end of cell division life thereof, the telomere DNA in the cells becomes gradually unstable, and at last it could not keep the chromosome stability to lead to apoptosis (M2 stage).

On the other hand, an enzyme "telomerase" having the ability to extend the sequence of telomere exists in cancer cells, in which the telomere chain having been shortened through cell division is prolonged by the enzyme. It is therefore said that cell growth may repeat endlessly in cancer cells. Because of this reason, it is believed that, different from normal cells, cancer cells abnormally repeat their growth not undergoing the above-mentioned M1 stage and M2 stage. Given that situation, it is expected that a compound capable of inhibiting the telomere chain extension to be effected by the telomerase peculiar to cancer cells could be a carcinostatic agent of the coming generation.

Telomerase is a reverse transcriptase having the ability to extend the single-stranded moiety of a telomere DNA, and contains inside it a complementary chain template RNA that corresponds to 1.5 times TTAGGG. Telomerase acts for chain extension based on the template RNA serving as a primer.

It is known that the telomere chain forms a quadraplex of four DNAS. It is believed that, when the quadraplex structure of the telomere chain could be stabilized, then the telomere chain extension to be caused by telomerase might be inhibited, and members of many study groups in the world are now studying the matter.

On the other hand, since telomerase after all extends the single-stranded part of telomere DNA as so mentioned hereinabove, we, the present inventors have had an inspiration that the telomerase activity might be inhibited if the single-stranded part of telomere DNA could be stabilized as a duplex structure such as a hairpin structure. This our inspiration is a novel technical idea, basically different from the above-mentioned quadraplex structure stabilization.

However, the complementary sequence necessary for forming the hairpin structure for the single-stranded telomere chain is TA only, and even if a complementary chain is formed for the part of "TA" as in the following, some base mismatches such as G-G mismatch will occur before and after the thus-formed complementary chain.

The above-mentioned sequence is to schematically show the 3'-terminal side single-stranded part of telomere that has formed a hairpin structure. Concretely, the right-hand side of the sequence is a loop moiety of the hairpin structure and is single-stranded as a whole. The 5'-side of the single-stranded telomere terminal is a duplex DNA, and the 3'-side thereof is the end of telomere, or that is, the end of chromosome. The vertical lines in the above-mentioned sequence mean that the indicated parts are complementary to each other, but the other parts are mismatches.

As in the above, it is generally difficult to form a stable hairpin structure in the single-stranded part of telomere, and in cancer cells, telomerase acts on the single-stranded part of telomere to thereby extend the telomere chain. However, if the base mismatches such as G-G mismatch could be solved in the single-stranded part of telomere, a stable hairpin structure could be formed in the single-stranded part of telomere and the telomerase activity on that part could be inhibited.

We, the present inventors have developed a bulge DNA recognition molecule that specifically binds to a DNA (bulge DNA) having an unpaired base (bulge base) to be formed in a duplex DNA to thereby stabilize it (Japanese Patent Application No. 11-262205). The bulge recognition molecule does not only bind to such an unpaired base through hydrogen bonding therebetween but also intercalates into the space formed by the presence of the bulge base, based on the stacking interaction between the aromatic ring of the molecule and the base around the bulge, and the molecule thereby stabilizes the bulge base.

We, the present inventors have further studied the action on the unpaired bases that is based on the stacking effect of the peripheral bases around them, and, as a result, have found that a compound having two different molecules each capable of forming a pair with a base can be relatively stably taken even in the site of base pair mismatches owing to the stacking effect as above, and have succeeded in providing a reagent capable of detecting and identifying the mismatched base sequences (Japanese Patent Application No. 11-336620).

DISCLOSURE OF THE INVENTION

The present invention is to provide a method of forming a stable hairpin structure, quadraplex structure or the like in single-stranded DNA, RNA or other nucleic acids having a mismatch sequence, by the use of such a reagent capable of detecting and identifying mismatched base pairs in such nucleic acids.

The invention is also to provide a method for inhibiting the activity of telomerase by forming a stable hairpin structure, quadraplex structure or the like in a single-stranded telomere chain, and to provide a method for inhibiting the growth of cancer cells and a cancer growth inhibitor.

BRIEF DESCRIPTION OF THE DRAWINGS

In FIG. 5, 1 indicates the case not having the molecule; 2 indicates the case having the molecule added thereto; and the arrow indicates the direction of the spectral change.

BEST MODES OF CARRYING OUT THE INVENTION

Figure 1:
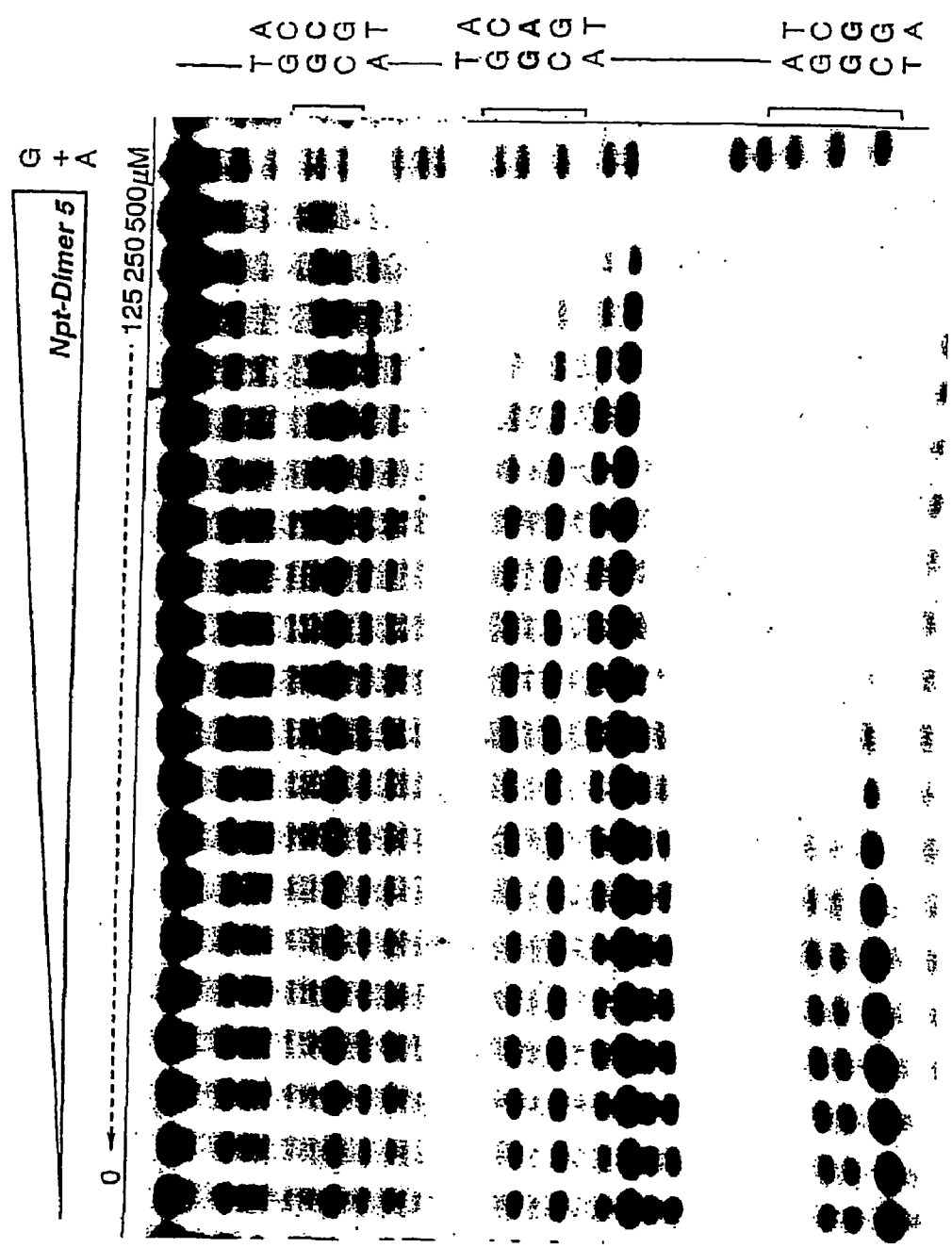
FIG. 1 is a photographic picture presented herewith in place of a drawing, and this shows the effect of the mismatch recognition molecule of the invention that inhibits the cleavage of mismatched sites by DNase I. The oligonucleotides are shown in SEQ ID NOS 5 & 2, 6 & 3 and 7 & 4, respectively, in order of appearance.

We, the present inventors have reached a novel technical idea that the telomerase effect could be inhibited by stabilizing the single-stranded part of a telomere DNA as a duplex structure such as a hairpin structure or the like. On the basis of such a novel technical idea, we have specifically noted a technique of stabilizing the base mismatches, especially the G-G mismatch in the single-stranded part of the telomere DNA having a hairpin structure, quadraplex structure or the like. In that situation, we have further made various experiments to confirm as to whether the G-G and other base mismatch recognition molecules that we have previously reported may bind to telomere chain at high affinity. As a result, we have found, as expected so, that a naphthyridine duplex which is a G-G mismatch recognition molecule binds to telomere chain to a great extent and, in addition, it significantly changes the structure of telomere chain.

The present invention relates to a method of forming a mimetic base pair of a base pair that fails to form any normal base pair among the base pairs of a single-stranded oligonucleotide chain by the use of a compound which has a chemical structural moiety A capable of forming any one base pair, a chemical structural moiety B capable of forming another base pair, and a linker moiety L that binds the chemical structure moieties A and B and which is represented by the following general formula (I):

A—L—B     (I)

wherein A represents a chemical structural moiety capable of forming a pair with one base of a base pair that fails to form a normal base pair; B represents a chemical structural moiety capable of forming a pair with the other base of that base pair failing to form a normal base pair; and L represents a linker structure that binds the chemical structures A and B. The invention also relates to a method of forming the above-mentioned mimetic base pair in a single-stranded oligonucleotide chain to thereby stabilize the unstable base pair therein not capable of forming a normal base pair, and relates to a stabilizer which comprises the compound and which is for stabilizing the unstable base pair not capable of forming a normal base pair.

The invention further relates to an inhibitor of inhibiting the activity of an enzyme that synthesizes a complementary chain to an oligonucleotide chain, and the enzyme activity inhibitor comprises a compound which may form a mimetic base pair of a base pair that fails to form a normal base pair among base the pairs of a single-stranded oligonucleotide and which is represented by the following general formula (I):

A—L—B     (I)

wherein A represents a chemical structural moiety capable of forming a pair with one base of a base pair that fails to form a normal base pair; B represents a chemical structural moiety capable of forming a pair with the other base of that base pair failing to form a normal base pair; and L represents a linker structure that binds the chemical structures A and B. The invention still further relates to a method of using the enzyme inhibitor for inhibiting the enzyme activity.

The invention also relates to a pharmaceutical composition comprising the compound which may form a mimetic base pair of a base pair that fails to form a normal base pair among the base pairs of a single-stranded oligonucleotide and which is represented by the following general formula (I):

A—L—B  (I)

wherein A represents a chemical structural moiety capable of forming a pair with one base of a base pair that fails to form a normal base pair; B represents a chemical structural moiety capable of forming a pair with the other base of that base pair failing to form a normal base pair; and L represents a linker structure that binds the chemical structures A and B, and a pharmaceutically-acceptable carrier. Preferably, the invention relates to such a pharmaceutical composition for curing, preventing or treating diseases, which inhibits the activity of the enzyme that synthesizes a complementary chain to an oligonucleotide chain to thereby cure, prevent or treat the intended diseases.

In the following description, the "chemical structure moiety capable of forming a pair with any one base of a base pair that fails to form a normal base pair (the moiety A and/or B in formula (I))" will be hereinafter simply referred to as a "base recognition site".

The present inventors have developed bulge DNA recognition molecules that specifically bind to the unpaired base (bulge base)—having DNA (bulge DNA) to be formed in a duplex DNA for stabilizing it (Japanese patent Application No. 11-262205). The bulge recognition molecule of the type intercalates and is stabilized in the space to be formed by the presence of the bulge base, based on the stacking interaction between the aromatic ring of the molecule and the base around the bulge. We, the present inventors have bound two such bulge recognition molecules with a binding chain such as a linker or the like, and have found that the individual bulge recognition molecules each form a base pair like the bulge base in the mismatch site of the base pair and that both the bulge recognition molecules are relatively stably taken in the duplex chain of DNA or RNA. Having utilized the properties of the bulge recognition molecules, we have developed a mismatch recognition molecule capable of specifically identifying a mismatched base pair in hybridized nucleic acids in a simplified manner (Japanese Patent Application No. 11-336620).

The present invention relates to an application of the mismatch recognition molecule that we the present inventors have heretofore developed, and the invention provides a method of forming a stable mimetic base pair in a single-stranded oligonucleotide chain by the use of the mismatch recognition molecule. Concretely, the method comprises stabilizing the mismatch base pair not capable of forming a normal base pair in a single-stranded oligonucleotide chain that could not have a stable duplex structure such as a stable hairpin structure because of the presence of the base pair not capable of forming a normal base pair. The invention also provides a method of inhibiting the activity of an enzyme that synthesizes a complementary oligonucleotide chain to the above-mentioned single-stranded oligonucleotide, and the method comprises forming the mimetic base pair to thereby form a relatively stable duplex structure such as a hairpin structure. The invention further provides a pharmaceutical composition capable of inhibiting the activity of the enzyme that synthesizes the complementary oligonucleotide chain to thereby cure, prevent and treat the enzyme-related various diseases.

Next described are the methods of the invention. Prior to describing them, the mismatch recognition molecule will be described below.

In one example, we the present inventors have produced a dimer of the following formula (III), for which we used a 1,8-naphthyridine derivative capable of forming a hydrogen bond to guanine and capable of being stabilized by the stacking effect of the bases around it.

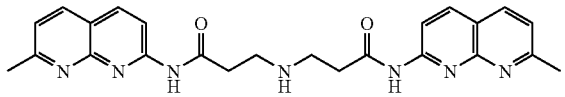

(III)

The compound forms a pair with guanine at the 1,8-naphthyridine moiety. In case where guanine is a bulge base, there is a plenty of space for forming therein a pair of that guanine with the 1,8-naphthyridine derivative, and therefore the formation of the pair of the 1,8-naphthyridine derivative and the bulge base will be good so far as the stability of the two is taken into consideration. However, in a mismatch case, some other base exists in the site in which the intended pair is to be formed, and therefore there is not so much space for the pair formation therein. In this case, the matter as to whether or not such a relatively large molecule could stably get in such a narrow space between the neighboring bases is a serious problem.

Accordingly, in such a case where a guanine-guanine mismatch is in a duplex structure of nucleic acid, we the present inventors have investigated as to whether or not the compound having two 1,8-naphthyridine moieties could form a pair with each mismatched guanine so as to be taken into the chain of the nucleic acid.

A 5'-$^{32}$P-labeled 52-mer duplex DNA having a GC base pair, GA mismatch base pair and a GG mismatch base pair in the duplex DNA was prepared. The partial listing of the corresponding moieties is shown below.

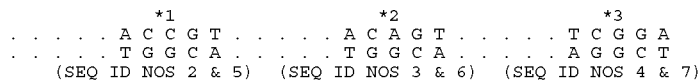

```
        *1              *2              *3
.....A C C G T.....A C A G T.....T C G G A
.....T G G C A.....T G G C A.....A G G C T
   (SEQ ID NOS 2 & 5)  (SEQ ID NOS 3 & 6)  (SEQ ID NOS 4 & 7)
```

In the above-mentioned duplex DNA, the moiety indicated by *1 is a normal G-C base pair; the moiety indicated by *2 is a G-A mismatch base pair; and the moiety indicated by *3 is a G-G mismatch base pair.

The inventors have analyzed the duplex DNA through DNase I (DNA hydrolase) footprinting titration for the sites where the DNA cleavage by DNase I was inhibited in the presence of a varying concentration of the compound of formula (III).

The results are in FIG. 1. FIG. 1 is a photographic picture presented herewith for showing the result of electrophoresis of the DNA samples.

In FIG. 1, the concentration of the compound of formula (III) varies from 0 to 500 μM from the left to the right. The sites cleaved with the DNase I (DNA hydrolase) are seen black, while those protected from cleavage with the DNase I are seen white.

For example, the normal G-C base pair is kept black even though the concentration of the compound of formula (III) is increased. This means that the normal G-C base pair is cleaved by DNase I. As opposed to this, however, the mismatch G-G site becomes gradually white with the increase in the concentration of the naphthyridine derivative of formula (III). This means that the compound of formula (III) inhibited the cleavage of the mismatch G-G site by the hydrolase. The same change is also seen in the lane of the G-A mismatch site where the concentration of the naphthyridine derivative is high.

The DNA cleavage inhibition against the DNA hydrolase depends on the presence (and also the concentration) of the compound of formula (III), and it will be peculiar to the compound of formula (III).

Figure 2:
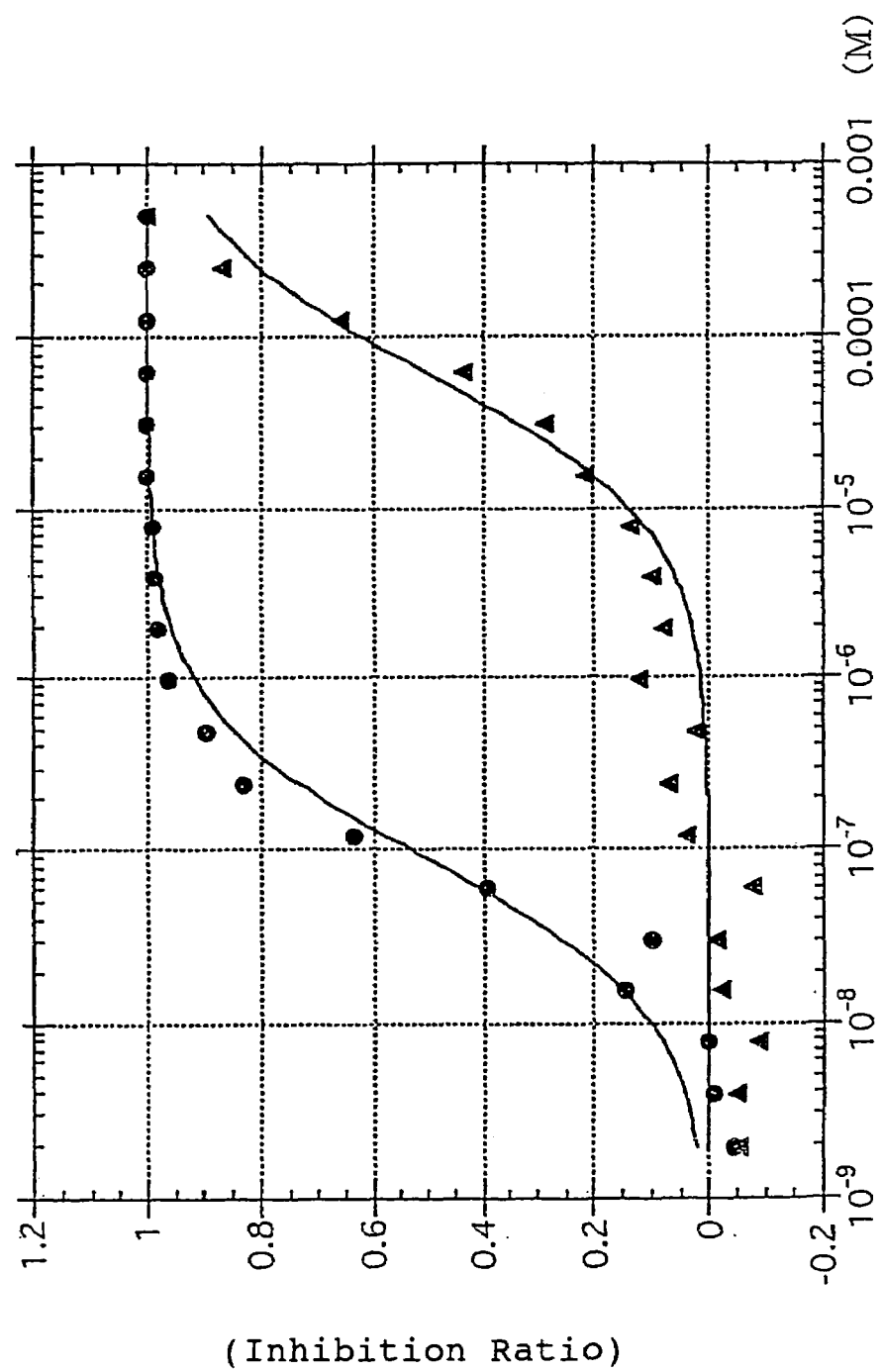
FIG. 2 is a graph showing the effect of the mismatch recognition molecule of the invention that inhibits the cleavage by DNase I.

The relationship between the cleavage band intensity and the naphthyridine concentration in FIG. 1 is plotted to give a graph as in FIG. 2. The vertical axis of FIG. 2 indicates the cleavage inhibition ratio derived from the cleavage band intensity. On this, 0.0 means that the base pair was almost completely cleaved, and 1.0 means that the base pair was almost completely protected from cleavage. The horizontal axis of FIG. 2 indicates the concentration (M) of the compound of formula (III) added to the test system. In FIG. 2, the closed circles (●) indicate the G-G mismatch site, and the closed triangles (▲) indicate the G-A mismatch site.

As is obvious from the graph of FIG. 2, it is understood that the compound of formula (III) is effective for inhibiting the cleavage of the G-G mismatch site even though its concentration is relatively low and it almost completely inhibited the G-G mismatch site cleavage when its concentration reached about $10^{-5}$ M. On the other hand, it is also understood that the compound of formula (III) becomes effective for inhibiting the cleavage of the G-A mismatch site when its concentration reached about $10^{-6}$ M or so and its effect of inhibiting the mismatch site cleavage is about 90% when its concentration reached $5 \times 10^{-3}$ M (500 μM).

From these results, the association constant of the compound of formula (III) to the G-G mismatch (Ka(GGmis)) is derived to be $1.13 \times 10^7$ M$^{-1}$. Similarly, the association constant of the compound of formula (III) to the G-A mismatch (Ka(GAmis)) is derived to be $1.63 \times 10^4$ M$^{-1}$.

The ratio of the association constants of the two ((Ka(GGmis))/(Ka(GAmis))) is 696. From this, it is understood that the compound of formula (III) specifically acts on the G-G mismatch site. The association constant of the compound of formula (III) to the G-G mismatch base pair is on the order of $10^7$ and is relatively large, and this indicates that the compound of formula (III) is much more stably taken in the G-G mismatch base pair site beyond all expectations.

The mismatch base recognition molecule thus having been taken in the duplex DNA forms a relatively stable pair, and it is believed that the pair formation by the molecule will lead to novel formation of a base pair sequence that any natural enzyme could not recognize.

Figure 3:
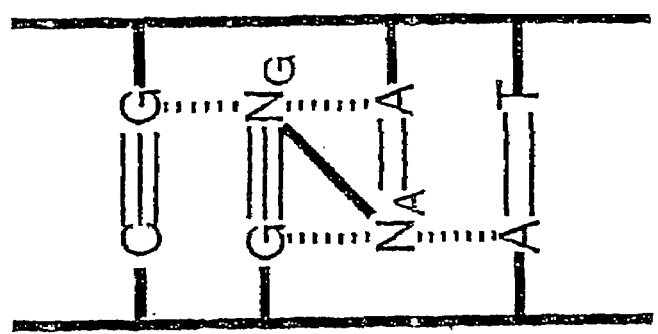
FIG. 3 schematically shows the action of the mismatch recognition molecule of the invention for mismatched sites.
Figure 3:
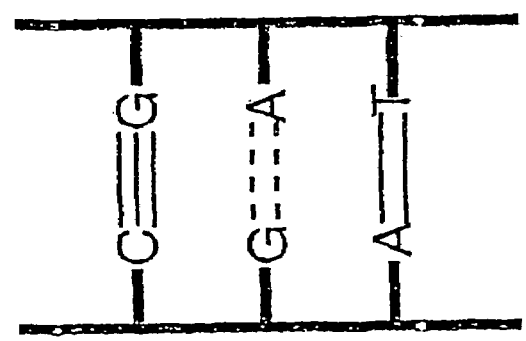

FIG. 3 schematically shows the situation of the compound of formula (I) of the invention (mismatch recognition molecule) that is relatively stably taken in the mismatch site of a base.

The left side of FIG. 3 shows the presence of G-A mismatch in a duplex DNA. In the other place of this DNA, normal base pairs are formed, and only the G-A site is mismatched. As a whole, however, the DNA is hybridized. When a mismatch recognition molecule of $N_A$-$N_G$ of the invention is added thereto, the DNA will change to the right hand of FIG. 3. Concretely, guanine (G) of the mismatch base forms a pair with the guanine recognition site ($N_G$) of the mismatch recognition molecule, while, on the other hand, adenine (A) of the other mismatch base forms a pair with the adenine recognition site ($N_A$) of the mismatch recognition molecule. In that condition, it is believed that the guanine recognition site ($N_G$) and the adenine recognition site ($N_A$) of the mismatch recognition molecule will bind to each other via a linker (-) having a suitable length and a suitable degree of freedom and they will be taken in the chain of the duplex DNA almost in the same manner as that of the other normal base pairs (see the right side of FIG. 3).

Another significant reason why the mismatch recognition molecule of the invention is relatively stably taken in the chain of such a duplex DNA is because the base recognition sites of the mismatch recognition molecule (for example, the guanine recognition site ($N_G$) and the adenine recognition site ($N_A$) in the above-mentioned case) are stabilized by the stacking effect (this may be considered as intermolecular force of neighboring bases) of the bases existing before and after them. On the right side of FIG. 3, the dotted lines indicate the stacking effect of the neighboring bases. One factor to produce the stacking effect will be the interaction of π-electrons (π-stacking effect). Therefore, the stacking effect may vary in some degree depending on the type of the bases before and after the base recognition sites, but it does not extremely lower the binding of the molecule of the invention to the mismatch sites.

Accordingly, the base recognition sites of the mismatch recognition molecule of the invention (the chemical structural moieties A and B in formula (I)) must be so designed that not only they can form a hydrogen bond to the intended base but also they can enjoy the stacking effect with the bases around and before and after them.

As in the above, the compound of formula (I) of the invention is so designed that it has two base recognition sites bound to each other via a linker having a suitable length and a suitable degree of freedom, and it is not limited to only the G-G mismatch exemplified in the above-mentioned case.

The above-mentioned case is to concretely demonstrate one example of guanine(G)-guanine(G) mismatch, and the mismatch recognition molecule used in this case has a base recognition site of a 1,8-naphthyridine derivative capable of forming a stable hydrogen bond to the guanine base. However, the mismatch recognition in the invention is not limited to the G-G mismatch as in the illustrated case. The base recognition site in the mismatch recognition molecule for use in the invention may be any and every one capable of recognizing one base of a mismatched base pair to thereby form a Watson-Crick base pair with that one base and capable of enjoying the stacking effect with the bases around it, and it can form base pairs with various types of bases not limited to guanine in the illustrated case.

For example, for the base recognition site for a mismatched base cytosine, usable are 2-aminonaphthyridin-4-one and its derivatives; for that for adenine, usable 2-quinolone derivatives such as 3-(2-aminoethyl)-2-quinolone and its derivatives; and for that for thymine, usable are 2-aminonaphthyridin-7-one and its derivatives.

It is desirable that the base recognition site in the mismatch recognition molecule for use in the invention, which is specifically recognized by a specific mismatched base, has a hydrogen-bonding site for forming a hydrogen bond and a planar-structured heterocyclic aromatic group that may be stacked on the neighboring bases. More preferably, the heterocyclic aromatic group in that site has a substituent with some steric hindrance for further reinforcing the selectivity to the specific base.

The substituent of the type includes, for example, a linear or branched alkyl group having from 1 to 15, preferably from 1 to 10, more preferably from 1 to 7 carbon atoms, an alkoxy group of which the alkyl moiety is linear or branched and has from 1 to 15, preferably from 1 to 10, more preferably from 1 to 7 carbon atoms, and a mono- or dialkylamino group of which the alkyl substituent is linear or branched and has from 1 to 15, preferably from 1 to 10, more preferably from 1 to 7 carbon atoms.

One or more carbon atoms in these alkyl, alkoxy and mono- or dialkylamino groups may be substituted with any of oxygen and nitrogen atoms.

The linker moiety L in the compound of formula (I) for use in the invention is not specifically defined so far as it binds the two base recognition sites via a suitable length and gives them a suitable degree of freedom. For example, it is a linear or branched, saturated or unsaturated alkylene group having from 1 to 20, preferably from 1 to 15, more preferably from 1 to 12 carbon atoms, in which one or more carbon atoms may be substituted with any of oxygen and nitrogen atoms or a carbonyl group. One preferred example of the linker has amido bonds at both ends thereof and has a nitrogen atom in the center part thereof, as in the compound of formula (III) mentioned above.

The linker moiety binds not only the two base recognition sites of the compound but also the branch that may extend from the linker so as to fix the compound to a carrier. For example, a branch of an alkylene group having a functional group at its end for binding the compound to a carrier may extend from the site of the nitrogen atom at around the center part of the linker, and the compound may be optionally fixed to a carrier via the branch, if desired.

The binding of the base recognition site A or B to the linker moiety L in the compound of formula (I) for use in the invention may be a carbon-carbon bond, but is preferably a bond with a functional group as the compound of the type is easy to produce. The bond with a functional group may be selected from various types of bonds, such as ether bond, ester bond, amido bond and phosphoryl bond. Of those, preferred is amido bond.

One preferred example of the compound of formula (I) of the invention, the mismatch base recognition molecule for G-G mismatch is a compound of the following general formula (II) and its fixed substances.

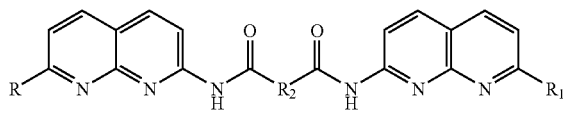

(II)

wherein R and $R_1$ each represent a hydrogen atom, an alkyl group having from 1 to 15 carbon atoms of which one or more carbon atoms may be substituted with any of oxygen and nitrogen atoms, an alkoxy group having from 1 to 15 carbon atoms of which one or more carbon atoms may be substituted with any of oxygen and nitrogen atoms, or a mono- or dialkylamino group having from 1 to 15 carbon atoms of which one or more carbon atoms of the alkyl moiety may be substituted with any of oxygen and nitrogen atoms; and $R_2$ represents an alkylene group having from 1 to 20 carbon atoms of which one or more carbon atoms may be substituted with any of oxygen and nitrogen atoms or a carbonyl group.

The "fixed substance" referred to herein means that the compound is fixed to a carrier or the compound has a "branch" via which it may be fixed to a carrier.

The alkylene group for $R_2$ is a divalent alkylene group as in formula (II).

The mismatch base recognition molecule of the invention may be used herein by itself, but it may be labeled in any desired manner for use herein. For example, a radioactive element is introduced into the linker moiety or into the branch extending from the linker for the molecule fixation, or a chemoluminescent or fluorescent molecule is introduced thereinto for labeling the molecule. Apart from it, the nucleic acid moiety of DNA or RNA to be detected may be labeled for labeling in detection.

Also if desired, a polymer material such as polystyrene may be bonded to a suitable site of the mismatch base recognition molecule of the invention either directly or via an alkylene group therebetween, and it may be fixed to a carrier.

The mismatch base recognition molecule of the invention is a low-molecular organic compound and is suitably produced in any ordinary manner for organic synthesis. For example, the 1,8-naphthyridine derivatives mentioned above may be produced by reacting 2-amino-1,8-naphthyridine or 2-amino-7-methyl-1,8-naphthyridine with a reactive derivative of an N-protected 4-aminobutyric acid such as an acid chloride thereof to thereby acylate the 2-amino group thereof, followed by deprotecting the amino-protective group of the resulting product. The protective group may be any and every amino-protective group generally used in peptide synthesis, including, for example, hydrochloride, and acyl and alkoxycarbonyl groups.

Thus prepared, the base recognition site is reacted with a linker compound that has a carboxyl group or its reactive derivative group at both ends thereof to thereby obtain the intended mismatch base recognition molecule. In the process where a reactive group such as a nitrogen atom is in the molecule for the linker compound, the reactive group may be suitably protected with a protective group such as that mentioned above.

The invention provides a method of forming a stable mimetic base pair in a single-stranded oligonucleotide chain by the use of the mismatch recognition molecule. Concretely, the method comprises stabilizing the mismatch base pair not capable of forming a normal base pair in a single-stranded oligonucleotide chain that could not have a stable duplex structure such as a stable hairpin structure because of the presence of the base pair not capable of forming a normal base pair. The single-stranded oligonucleotide chain may be any of mRNA and rRNA that are single-stranded as a whole. Apart from it, the chain may partly have a duplex structure such as a hairpin structure, or may also be a single-stranded oligonucleotide chain that forms the end part of a duplex DNA not terminated with a blunt end.

For example, in the telomere region that forms the end part of a chromosome of an eukaryotic cell, several tens of terminal bases form a single-stranded structure, and this part that comprises them may be the single-stranded oligonucleotide chain for use in the invention.

In the single-stranded telomere chain, the complementary sequence necessary for forming the intended hairpin structure is the TA part alone, and even if a complementary chain is formed for the part of "TA" as in the following, some base mismatches such a G-G mismatch will occur before and after the thus-formed complementary chain.

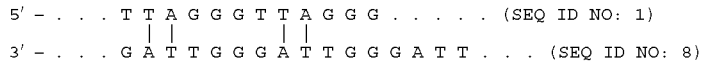

The above-mentioned sequence is to schematically show the 3'-terminal side single-stranded part of telomere that has formed a hairpin structure. Concretely, the right-hand side of the sequence is a loop moiety of the hairpin structure and is single-stranded as a whole. The 5'-side of the single-stranded telomere terminal is a duplex DNA, and the 3'-side thereof is the end of telomere, or that is, the end of chromosome. The vertical lines in the above-mentioned sequence mean that the indicated parts are complementary to each other, but the other parts are mismatches.

We, the present inventors have considered that, in the single-stranded part of the telomere sequence, if the mismatches, G-G mismatch and/or G-T mismatch could form mimetic base pairs by the use of the above-mentioned mismatch recognition molecule, a stable hairpin structure could be formed in the single-stranded part of the telomere sequence. Given that situation, we, the present inventors tried the mismatch recognition molecule of formula (III) mentioned above for human telomere. Our experiment is as follows:

Samples of single-stranded human telomere sequence DNA were tested for the inhibition of DNA cleavage by DNase I (DNA hydrolase) through footprinting titration in the presence of a varying concentration of the compound of formula (III) (this is hereinafter referred to as naphthyridine dimer or simply as ND).

Figure 4:
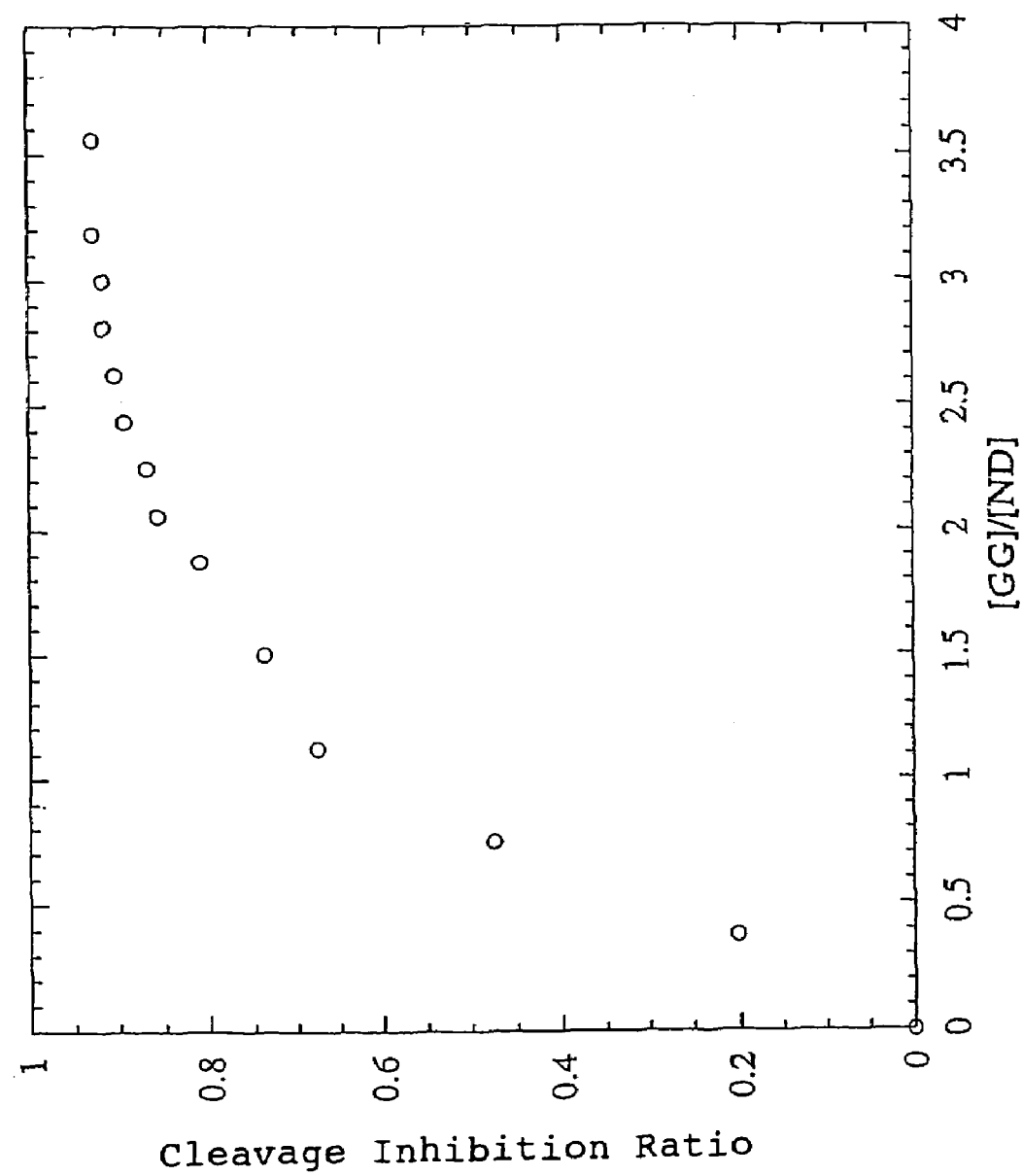
FIG. 4 is a graph showing the effect of the mismatch recognition molecule of the invention that inhibits the cleavage of a telomere chain-having single-stranded DNA by DNase I.

The result is shown in FIG. 4. The test result in FIG. 4 is similar to that in FIG. 2. The vertical axis of FIG. 4 indicates the cleavage inhibition ratio derived from the cleavage band intensity. On this, 0.0 means that the base pair was almost completely cleaved, and 1.0 means that the base pair was almost completely protected from cleavage. The horizontal axis of FIG. 4 indicates the ratio of the G-G mismatch concentration to the concentration (M) of the compound of formula (III) added to the test system, [GG]/[ND] in which ND means the compound of formula (III).

As is obvious from the graph of FIG. 4, it is understood that the compound of formula (III) is effective for inhibiting the cleavage of the G-G mismatch site even though its concentration is relatively low ([GG]/[ND]=0.5) and it almost completely inhibited the G-G mismatch site cleavage when the concentration ratio [GG]/[ND] reached about 3.

From the results, the association constant of the compound of formula (III) to the G-G mismatch (Ka(GGmis)) is derived to be $4.2 \times 10^5$ $M^{-1}$.

The data indicates that the compound of formula (III) is much more stably taken in the G-G mismatch base pair site beyond all expectations. It is understood that the compound forms a relatively stable pair in the G-G mismatch site in the single-stranded telomere, and the pair formation by the compound has led to formation of a base pair that any natural enzyme could not recognize.

Figure 5:
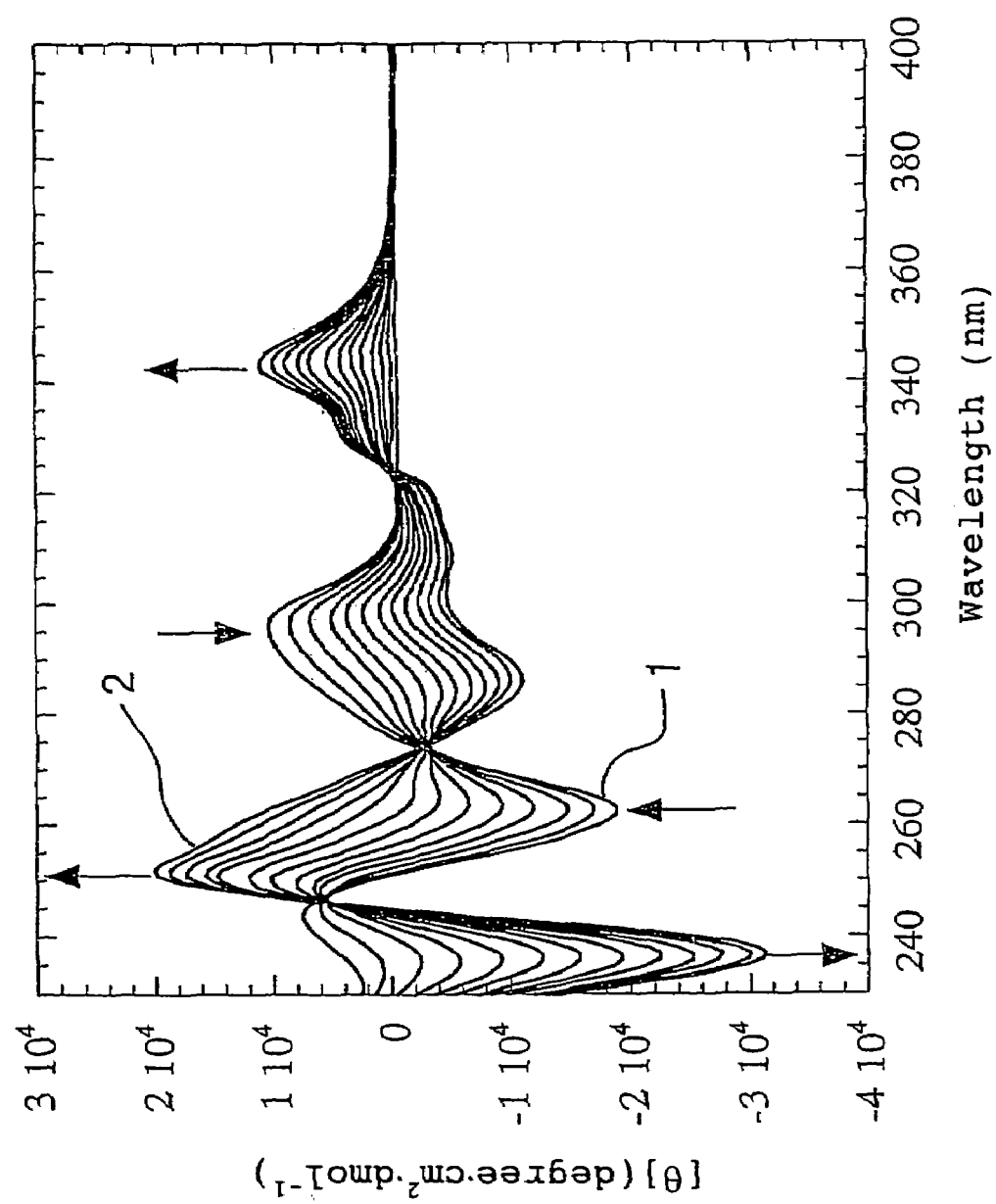
FIG. 5 shows various CD spectral changes in a telomere chain-having single-stranded DNA in the presence or absence of a varying concentration of the mismatch recognition molecule of the invention.

The telomere structure change to be caused by the addition of the compound of formula (III) (naphthyridine dimer) to the structure was investigated through CD spectrometry. The result is shown in FIG. 5. In FIG. 5, 1 indicates the CD spectrum of human telomere alone, and 2 indicates the CD spectrum of human telomere with naphthyridine dimer added thereto. The vertical axis indicates the angle θ (degree·cm²·dmol⁻¹); and the horizontal axis indicates the wavelength (nm).

As in FIG. 5, the CD spectrum of the sample human telomere greatly varied with addition of the naphthyridine dimer to the sample, and this means that the addition of the naphthyridine dimer to the sample has greatly changed the telomere structure.

The structure of human telomere, especially the structure of the single-stranded part thereof has not as yet fully clarified, but it is believed that the structure will be a hairpin structure or a quadraplex structure. However, even the structure of the type could not form a satisfactory base pair necessary for stabilizing the structure, and it readily returns to a single-stranded structure by the action of telomerase thereon. This means that the terminal chain of telomere readily extends by the action of telomerase thereon.

As so mentioned hereinabove, when the mismatch recognition molecule of the invention is added to the terminal part of telomere, then it may form mimetic base pairs even at ordinary mismatch base pairs (e.g., G-G mismatch) in that part, and, accordingly, the hairpin structure or the quadraplex structure formed by some base pairs can be stabilized by the formation of the mimetic base pair to such a degree that any enzyme could not act on the thus-stabilized structure. As a result, the telomere terminal is prevented from being extended by telomerase acting thereon, and the cells with no telomere chain extension could no more grow and will soon die. This means the stop of growth, or that it, the death of cancer cells like that of normal cells.

In the above-mentioned description, concretely demonstrated is one case of G-G mismatch for the mismatch recognition molecule of the invention. The same as above shall apply to any other cases such as T-G mismatch when the moieties A and B in the mismatch recognition molecule of formula (I) are replaced with any others capable of forming base pairs with any other bases.

FIG. 3 schematically shows the situation of the mismatch recognition molecule of formula (I) of the invention that is relatively stably taken in the mismatch site of a base.

The left side of FIG. 3 shows the presence of G-A mismatch in a duplex DNA. In the other place of this DNA, normal base pairs are formed, and only the G-A site is mismatched. As a whole, however, the DNA is hybridized. When a mismatch recognition molecule of $N_A$-$N_G$ of the invention is added thereto, the DNA will change to the right hand of FIG. 3. Concretely, guanine (G) of the mismatch base forms a pair with the guanine recognition site ($N_G$) of the mismatch recognition molecule, while, on the other hand, adenine (A) of the other mismatch base forms a pair with the adenine recognition site ($N_A$) of the mismatch recognition molecule. In that condition, it is believed that the guanine recognition site ($N_G$) and the adenine recognition site ($N_A$) of the mismatch recognition molecule will bind to each other via a linker (-) having a suitable length and a suitable degree of freedom and they will be taken in the chain of the duplex DNA almost in the same manner as that of the other normal base pairs (see the right side of FIG. 3).

The "mimetic base pair" referred to herein is meant to indicate a base pair that differs from any naturally-existing base pair, and this does not mean the intensity of a base pair. The "normal base pair" also referred to herein is meant to indicate a naturally-existing base pair, including base pairs of G-C, A-T and A-U.

The present invention is based on the novel technical idea that a mimetic base pair which could not be formed in an ordinary condition is formed in a single-stranded oligonucleotide chain such as the terminal of telomere to thereby inhibit the activity of an enzyme that may synthesize the complementary chain to the single-stranded oligonucleotide chain. So far as it may inhibit the activity of the enzyme that synthesizes such a complementary chain, the mimetic base pair may be formed in any site of the single-stranded oligonucleotide chain. For example, it may be in a primer region or a region where chain extension goes on. The enzyme to synthesize such a complementary chain may be any DNA synthase such as DNA polymerase, or any RNA synthase such as RNA polymerase, or any reverse transcriptase.

For the enzyme activity inhibitor of the invention, one or more compounds of formula (I) may be used directly as they are, or they may be combined with any suitable carrier. If desired, the compounds may be modified with a substance having an affinity for the target cells so that the thus-modified compounds may specifically act on the target cells. Also if desired, the compounds may be modified with a suitable marker so that the real time condition of the DNA being processed with the marker-modified compound may be monitored.

The pharmaceutical composition of the invention may comprise one or more compounds of formula (I) directly as they are, or may contain them along with a suitable carrier. The carrier may be any and every one acceptable for pharmaceutical use. The pharmaceutical composition of the invention may be administered orally or parenterally.

The invention provides a novel concept that, in a single-stranded oligonucleotide chain that could not form a stable duplex or quadraplex structure because of the presence of a base pair mismatch therein, a "mimetic base pair" is formed in the mismatch site by the use of the mismatch recognition molecule of formula (I) to thereby form a stable duplex or quadraplex structure, and this leads to inhibition of the function of the single-stranded oligonucleotide chain, for example, inhibition of the activity of the enzyme that synthesizes a complementary chain to the single-stranded oligonucleotide chain to thereby finally cure, prevent and/or treat various diseases to be caused by the function of the single-stranded oligonucleotide chain. The invention therefore encompasses various concrete means of utilizing the concept and should not be limited to any specific means of utilizing it.

The invention is described in more detail with reference to the following experimental examples, which, however, are not intended to restrict the scope of the invention.

EXAMPLES

Example 1

Production of Compound of Formula (III)

The entitled compound was produced according to the chemical reaction mentioned below.

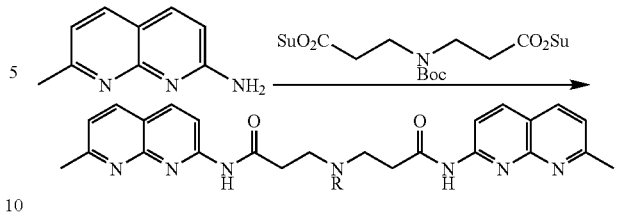

wherein Boc represents a t-butoxycarbonyl group.

N-Boc-protected succinimidyl dicarboxylate (313 mg, 0.74 mmols) was dissolved in chloroform (15 ml), to which was added 2-amino-7-methyl-1,8-naphthyridine (294 mg, 1.85 mmols). This was reacted for 48 hours at room temperature, and then post-processed to obtain a Boc-protected dinaphthyridinamide. This was dissolved in ethyl acetate that contains 4 N hydrochloric acid, and reacted for 2 hours at room temperature to give the entitled dinaphthyridinamide. The overall yield of the product is 13%.

$^1$H NMR (CD$_3$OD, 400 MHz) δ: 8.26 (d, 2H, J=8.8 Hz), 8.14 (d, 2H, J=8.8 Hz), 8.11 (d, 2H, J=8.0 Hz), 7.34 (d, 2H, J=8.0 Hz), 3.20 (t, 4H, J=6.0 Hz), 2,84 (t, 4H, J=6.0 Hz), 2,68 (s, 6H). FABMS (NBA), m/e (%): 444 [(M+H)$^+$] (10), 246 (40), 154 (100).

HRMS Calculated as C$_{24}$H$_{26}$O$_2$N$_7$ [(M+N)$^+$] 444.2146 Found 444.2148

Example 2

$^{32}$P-5'-end-labeled 52-mer DNA was hybridized into a duplex DNA with G-G and G-A mismatches (see the right side of FIG. 1).

A varying concentration of the compound obtained in Example 1 was added to the duplex DNA, and the DNA was analyzed through DNase I footprinting titration.

Concretely, the duplex DNA (<4 nM strand concentration) was incubated at 4° C. for 12 hours along with a varying concentration of the compound obtained in Example 1, in a tris-HCl buffer (10 mM, pH 7.6) that contains NaCl (100 mM) and MgCl$_2$(5 mM). To this was added 0.2 U DNaseI (DNA hydrolase), and this was further incubated at 25° C. for 8 minutes. Next, this was precipitated in ethanol to recover the DNA, which was then subjected to electrophoresis with a gel that contains 12% polyacrylamide and 7 M urea.

The result is shown in FIG. 1.

Example 3

A solution of a 22-mer oligonucleotide having the following base sequence:

5'-AGGGTTAGGGTTAGGGTTAGGG3' (SEQ ID NO: 9) in a sodium cacodylate buffer (10 mM, pH 7.0, NaCl 100mM) was heated at 70° C. for 5 minutes, and then gradually cooled so that the oligomer could form a quadraplex structure (see Structure, 263, 1 (1993)). A varying concentration of a naphthyridine dimer was dropwise added to the resulting solution, and the naphthyridine dimer-binding amount was obtained through 360 nm absorptiometry.

The result is shown in FIG. 4. The association constant of the dimer was derived from Scatchard Plot, and it was 4.2×10$^5$ M$^{-1}$.

Example 4

A solution of a 22-mer oligonucleotide having the following base sequence: 5'-AGGGTTAGGGTTAGGGTTAGGG3' (SEQ ID NO: 9) in a sodium cacodylate buffer (10 mM, pH 7.0, NaCl 100 mM) was heated at 70° C. for 5 minutes, and then gradually cooled so that the oligomer could form a quadraplex structure (see Structure, 263, 1 (1993)). A varying concentration (0 to 50 μM) of a naphthyridine dimer was added to the resulting solution, and then left at 7° C. for 5 minutes, and the circular dichroic spectrum (CD spectrum) of the sample was measured at that temperature.

The result is shown in FIG. 5. This confirms that the addition of the naphthyridine dimer to the oligomer significantly changes the spectral pattern of the oligomer in the arrowed direction as in FIG. 5. The spectrum change indicates that the oligomer DNA having had a quadraplex structure in the absence of the naphthyridine dimer significantly changed its structure with the addition of the naphthyridine dimer thereto.

Industrial Applicability

According to the method of the invention of using the mismatch recognition molecule of formula (I), a mimetic base pair may be formed in a single-stranded oligonucleotide chain, and a relatively stable duplex of quadraplex structure may be thereby readily formed in the single-stranded oligonucleotide chain in a simplified manner. Forming such a relatively stable structure in a single-stranded oligonucleotide chain interferes with the function of the single-stranded oligonucleotide. For example, it is effective for inhibiting the chain extension at the terminal of the telomere region in chromosome, and is therefore useful for curing, preventing and treating various diseases such as cancers to be caused by the function of the single-stranded oligonucleotide.

The invention claimed is:

1. A method for forming a mimetic base pair at a base pair that fails to form any normal base pair among the base pairs of a single-stranded oligonucleotide chain comprising the steps of:

(1) providing a compound represented by the formula A-L-B, wherein A represents a chemical structural moiety capable of forming a pair with one base of the base pair that fails to form a normal base pair, B represents a chemical structural moiety capable of forming, a pair with another base of the base pair that fails to form a normal base pair, and L represents a linker structure that binds the moieties A and B; and wherein said compound is characterized to form a mimetic base pair in a single-stranded oligonucleotide chain by a hydrogen bond formed between bases and the moieties A and B and a stabilization of the moieties A and B results from a stacking effect derived from the bases in the vicinity of the moiety B, and (2) forming the mimetic base pair at a base pair that fails to form a normal base pair among the base pairs of a single stranded oligonucleotide chain.

2. The method according to claim 1, wherein the chemical structural moieties A and B in the compound of formula (I) each have a heterocyclic aromatic group that contains at least two chemical structural moieties capable of forming a hydrogen bond to a base.

3. The method according to claim 2, wherein at least one of the chemical structural moeities A and B in the compound of formula (I) is naphthyridine or its derivative.

4. The method according to claim 1, wherein the binding of the chemical structural moieties A and B to the linker moiety L in the compound of formula (I) is a carbonamido bond.

5. The method according to claim 1, wherein the compound of formula (I) is a compound represented by the following formula (II):

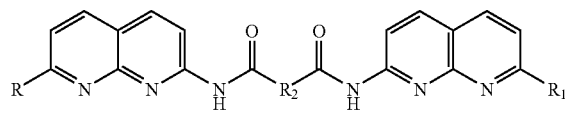
(II)

wherein R and $R_1$ each represent a hydrogen atom, and alkyl group having from 1 to 15 carbon atoms of which one or more carbon atoms may be substituted with any of oxygen and nitrogen atoms, an alkoxy group having from 1 to 15 carbon atoms of which one or more carbon atoms may be substituted with any of oxygen and nitrogen atoms, or a mono-or dialkylamino group having from 1 to 15 carbon atoms of which one or more carbon atoms of the alkyl moiety may be substituted with any of oxygen and nitrogen atoms; and $R_2$ represents an alkyone group having from 1 to 20 carbon atoms of which one or more carbon atoms may be substituted with any of oxygen and nitrogen atoms or a carbonyl group.

6. The method according to claim 1, wherein the oligonucleotide chain is a DNA chain.

7. The method according to claim 6, wherein the DNA chain is a DNA chain in the telomere region.

8. The method according to claim 1, wherein the base pair that fails to form a normal base pair among the base pairs in the single-stranded oligonucleotide chain is a G-G mismatch.

9. The method according to claim 1, wherein the structure of the mimetic base pair formed is a hairpin structure.

10. A method for stabilizing a base pair that fails to form any normal base pair among the base pairs of a single-stranded oligonucleotide chain, the method comprising the steps of:

(1) providing a compound represented by the formula A-L-B, wherein A represents a chemical structural moiety capable of forming a pair with one base of the base pair that fails to form a normal base pair, B represents a chemical structural moiety capable of forming, a pair with another base of the base pair that fails to form a normal base pair, and L represents a linker structure that binds the moieties A and B, where the compound is characterized to form a mimetic base pair in a single-stranded oligonucleotide chain by a hydrogen bond formed between a base and the moeity B and a stabilization of the moiety B resulting from a stacking effect derived from the bases in the vicinity of the moiety B, and (2) stabilizing the base pair that fails to form any base pair among the base pairs of the single-stranded oligonucleotide chain by forming the mimetic base pair in the single-stranded oligonucleotide chain.

11. A stabilizer for a base pair that fails to form any normal base pair among the base pairs of a single-stranded oligonucleotide chains, comprising a compound of the general formula:

A-L-B    (I)

wherein A represents a chemical structural moiety capable of forming a pair with one base of the base pair that fails to form a normal base pair; B represents a chemical structural moiety capable of forming a pair with the other base of that base pair failing to form a normal base pair; and L represents a linker structure that binds the chemical structure A and B, and wherein said compound (I) is characterized to form a mimetic base pair in a single-stranded oligonucleotide chain by a hydrogen bond formed between bases and the moieties A and B and a stabilization of the moeities A and B resulting from a stacking effect derived from the bases in the vicinity of the moieties A and B.

* * * * *